US012226219B1

United States Patent
Kim et al.

(10) Patent No.: US 12,226,219 B1
(45) Date of Patent: Feb. 18, 2025

(54) DETECTING NONSUSTAINED VENTRICULAR TACHYCARDIA IN A WEARABLE CARDIOVERTER DEFIBRILLATOR

(71) Applicant: West Affum Holdings Corp., Grand Cayman (KY)

(72) Inventors: Jaeho Kim, Redmond, WA (US); Joseph Sullivan, Kirkland, WA (US)

(73) Assignee: West Affum Holdings DAC, Dublin (IE)

( * ) Notice: Subject to any disclaimer, the term of this patent is extended or adjusted under 35 U.S.C. 154(b) by 113 days.

(21) Appl. No.: 17/193,924

(22) Filed: Mar. 5, 2021

Related U.S. Application Data

(60) Provisional application No. 63/068,781, filed on Aug. 21, 2020.

(51) Int. Cl.
*A61B 5/0245* (2006.01)
*A61B 5/00* (2006.01)
(Continued)

(52) U.S. Cl.
CPC .......... *A61B 5/366* (2021.01); *A61B 5/02455* (2013.01); *A61B 5/352* (2021.01);
(Continued)

(58) Field of Classification Search
CPC ......... A61B 5/363; A61B 5/366; A61B 5/352; A61B 5/02455; A61B 5/7246
See application file for complete search history.

(56) References Cited

U.S. PATENT DOCUMENTS

| | | |
|---|---|---|
| 3,724,455 A | 4/1973 | Unger |
| 4,583,524 A | 4/1986 | Hutchins |
| | (Continued) | |

FOREIGN PATENT DOCUMENTS

WO    1998039061 A2    9/1998

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

(Continued)

*Primary Examiner* — Jennifer Pitrak McDonald
*Assistant Examiner* — Adreanne A. Arnold
(74) *Attorney, Agent, or Firm* — Polsinelli PC

(57) ABSTRACT

In one embodiment, a method to monitor a patient's heart health is described. The method may include processing at least one electrocardiogram (ECG) signal and diagnosing an episode of nonsustained ventricular tachycardia (NSVT) based at least in part on the processing of the at least one ECG signal. In some embodiments, the NSVT episode may satisfy an NSVT time duration and a QRS criterion. The NSVT time duration may be between 5 seconds and 15 seconds. In some instances, the QRS criterion may be a temporary QRS template of two sequential incoming QRS complexes. In some embodiments, the method may determine a similarity between the temporary QRS template and at least two subsequent QRS complexes by calculating a feature correlation coefficient between the QRS template and the subsequent QRS complexes.

9 Claims, 12 Drawing Sheets

(51) Int. Cl.
  *A61B 5/352* (2021.01)
  *A61B 5/363* (2021.01)
  *A61B 5/366* (2021.01)
  *A61N 1/39* (2006.01)

(52) U.S. Cl.
  CPC ............ *A61B 5/363* (2021.01); *A61B 5/7246* (2013.01); *A61N 1/3904* (2017.08); *A61N 1/3943* (2013.01); *A61N 1/395* (2013.01); *A61N 1/3987* (2013.01)

(56) References Cited

U.S. PATENT DOCUMENTS

| | | | |
|---|---|---|---|
| 4,619,265 | A | 10/1986 | Morgan et al. |
| 4,928,690 | A | 5/1990 | Heilman et al. |
| 4,955,381 | A | 9/1990 | Way et al. |
| 5,078,134 | A | 1/1992 | Heilman et al. |
| 5,228,449 | A | 7/1993 | Christ et al. |
| 5,348,008 | A | 9/1994 | Bornn et al. |
| 5,353,793 | A | 10/1994 | Born |
| RE34,800 | E | 11/1994 | Hutchins |
| 5,394,892 | A | 3/1995 | Kenny |
| 5,405,362 | A | 4/1995 | Kramer et al. |
| 5,474,574 | A | 12/1995 | Payne et al. |
| 5,662,690 | A | 9/1997 | Cole et al. |
| 5,782,878 | A | 7/1998 | Morgan et al. |
| 5,792,204 | A | 8/1998 | Snell |
| 5,902,249 | A | 5/1999 | Yster |
| 5,913,685 | A | 6/1999 | Hutchins |
| 5,944,669 | A | 8/1999 | Kaib |
| 6,047,203 | A | 4/2000 | Sackner et al. |
| 6,065,154 | A | 5/2000 | Hulings et al. |
| 6,108,197 | A | 8/2000 | Janik |
| 6,148,233 | A | 11/2000 | Owen et al. |
| 6,201,992 | B1 | 3/2001 | Freeman |
| 6,263,238 | B1 | 7/2001 | Brewer et al. |
| 6,287,328 | B1 | 9/2001 | Snyder et al. |
| 6,304,780 | B1 | 10/2001 | Owen et al. |
| 6,319,011 | B1 | 11/2001 | Motti et al. |
| 6,334,070 | B1 | 12/2001 | Nova et al. |
| 6,356,785 | B1 | 3/2002 | Snyder |
| 6,427,083 | B1 | 7/2002 | Owen et al. |
| 6,437,083 | B1 | 7/2002 | Owen et al. |
| 6,529,875 | B1 | 3/2003 | Nakajima |
| 6,546,285 | B1 | 4/2003 | Owen et al. |
| 6,671,545 | B2 | 12/2003 | Fincke |
| 6,681,003 | B2 | 1/2004 | Linder et al. |
| 6,762,917 | B1 | 7/2004 | Verbiest et al. |
| 7,065,401 | B2 | 6/2006 | Worden |
| 7,559,902 | B2 | 7/2009 | Ting et al. |
| 7,865,238 | B2 | 1/2011 | Brink |
| 7,870,761 | B2 | 1/2011 | Valentine et al. |
| 7,974,689 | B2 | 7/2011 | Volpe et al. |
| 8,135,462 | B2 | 3/2012 | Owen et al. |
| 8,140,154 | B2 | 10/2012 | Donnelly et al. |
| 8,369,944 | B2 | 2/2013 | Macho et al. |
| 8,548,557 | B2 | 10/2013 | Garstka et al. |
| 8,615,295 | B2 | 12/2013 | Savage et al. |
| 8,644,925 | B2 | 2/2014 | Volpe et al. |
| 8,897,860 | B2 | 11/2014 | Volpe et al. |
| 8,904,214 | B2 | 12/2014 | Volpe et al. |
| 8,965,500 | B2 | 2/2015 | Macho et al. |
| 9,008,801 | B2 | 4/2015 | Kaib et al. |
| 9,089,685 | B2 | 7/2015 | Sullivan et al. |
| 9,131,901 | B2 | 9/2015 | Volpe et al. |
| 9,132,267 | B2 | 9/2015 | Kaib |
| 9,408,548 | B2 | 8/2016 | Volpe et al. |
| 9,454,219 | B2 | 9/2016 | Volpe et al. |
| 9,592,403 | B2 | 3/2017 | Sullivan |
| 2003/0158593 | A1 | 8/2003 | Heilman et al. |
| 2005/0107833 | A1 | 5/2005 | Freeman et al. |
| 2005/0107834 | A1 | 5/2005 | Freeman et al. |
| 2008/0312709 | A1 | 12/2008 | Volpe et al. |
| 2009/0005827 | A1 | 1/2009 | Weintraub et al. |
| 2010/0007413 | A1 | 1/2010 | Herleikson |
| 2010/0298899 | A1 | 11/2010 | Donnelly et al. |
| 2011/0022105 | A9 | 1/2011 | Owen et al. |
| 2011/0288604 | A1 | 11/2011 | Kaib et al. |
| 2011/0288605 | A1 | 11/2011 | Kaib et al. |
| 2012/0112903 | A1 | 5/2012 | Kaib et al. |
| 2012/0144551 | A1 | 6/2012 | Guldalian |
| 2012/0150008 | A1 | 6/2012 | Kaib et al. |
| 2012/0158075 | A1 | 6/2012 | Kaib et al. |
| 2012/0265265 | A1 | 10/2012 | Razavi et al. |
| 2012/0283794 | A1 | 11/2012 | Kaib et al. |
| 2012/0293323 | A1 | 11/2012 | Kaib et al. |
| 2012/0302860 | A1 | 11/2012 | Volpe et al. |
| 2012/0310315 | A1 | 12/2012 | Savage et al. |
| 2013/0085538 | A1 | 4/2013 | Volpe et al. |
| 2013/0231711 | A1 | 9/2013 | Kaib |
| 2013/0245388 | A1 | 9/2013 | Rafferty et al. |
| 2013/0274565 | A1 | 10/2013 | Langer et al. |
| 2013/0317852 | A1 | 11/2013 | Worrell et al. |
| 2013/0325078 | A1 | 12/2013 | Whiting et al. |
| 2014/0005988 | A1* | 1/2014 | Brockway .......... H03H 17/0248 703/2 |
| 2014/0025131 | A1 | 1/2014 | Sullivan et al. |
| 2014/0070957 | A1 | 3/2014 | Longinotti-Buitoni et al. |
| 2014/0163663 | A1 | 6/2014 | Poddar et al. |
| 2014/0324112 | A1 | 10/2014 | Macho et al. |
| 2014/0378812 | A1 | 12/2014 | Saroka et al. |
| 2015/0039053 | A1 | 2/2015 | Kaib et al. |
| 2015/0328472 | A1 | 11/2015 | Sullivan et al. |
| 2016/0004831 | A1 | 1/2016 | Carlson et al. |
| 2016/0082277 | A1 | 3/2016 | Foshee, Jr. et al. |
| 2016/0135706 | A1* | 5/2016 | Sullivan ................ A61B 5/316 600/509 |
| 2018/0348759 | A1* | 12/2018 | Freeman .............. A61N 1/3904 |
| 2021/0393966 | A1* | 12/2021 | Gunderson .......... A61N 1/3937 |

OTHER PUBLICATIONS

LIFECOR LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

\* cited by examiner

DETECTING NONSUSTAINED VENTRICULAR TACHYCARDIA IN A WEARABLE CARDIOVERTER DEFIBRILLATOR

CROSS REFERENCE TO RELATED PATENT APPLICATIONS

This patent application claims benefit of U.S. Provisional Patent Application No. 63/068,781 filed Aug. 21, 2020 and is incorporated herein by reference in their entirety for all purposes.

BACKGROUND

When people suffer from some types of heart arrhythmias, in some instances, blood flow to various parts of the body may be reduced. Some arrhythmias can result in a Sudden Cardiac Arrest (SCA). SCA can lead to death very quickly, e.g., within 10 minutes, unless treated in the interim. Some observers have thought that SCA is the same as a heart attack, which it is not.

Some people have an increased risk of SCA. Such people may include patients who have had a heart attack or a prior SCA episode. A frequent recommendation for these people is to receive an Implantable Cardioverter Defibrillator (ICD). The ICD is surgically implanted in the chest, and continuously monitors the patient's intracardiac electrogram (IEGM). If certain types of heart arrhythmias are detected, then the ICD delivers an electric shock through the heart.

As a further precaution, people who have been identified to have an increased risk of a SCA are sometimes given a Wearable Cardioverter Defibrillator (WCD) system to wear until an ICD is implanted. Early versions of such systems were called wearable cardiac defibrillator systems. A WCD system typically includes a harness, vest, belt, or other garment that the patient wears. The WCD system further includes electronic components, such as a defibrillator and electrodes, coupled to the harness, vest, or another garment. When the patient wears the WCD system, the electrodes may electrically contact the patient's skin, and aid in sensing the patient's electrocardiogram (ECG). If a shockable heart arrhythmia (e.g., ventricular fibrillation or VF) is detected from the ECG, then the defibrillator delivers an appropriate electric shock through the patient's body, and thus through the heart. The delivered shock may restart the patient's heart and save the patient's life.

BRIEF SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present disclosure describes instances and examples of cardiac monitoring systems (e.g., WCD systems), devices, systems, storage media that may store programs, and methods.

In one embodiment, a method to monitor a patient's heart health is described. The method may include processing at least one electrocardiogram (ECG) signal and diagnosing an episode of nonsustained ventricular tachycardia (NSVT) based at least in part on the processing of the at least one ECG signal.

In some embodiments, the NSVT episode may satisfy an NSVT time duration and a QRS criterion. The NSVT time duration may be between 5 seconds and 15 seconds. In some instances, the QRS criterion may be a temporary QRS template of incoming QRS complexes. In some embodiments, the method may determine a similarity between the temporary QRS template and at least two subsequent QRS complexes by calculating a feature correlation coefficient between the QRS template and the subsequent QRS complexes.

In some embodiments, the NSVT episode may exceed a heart rate threshold and an NSVT time threshold. The heart rate threshold may be 170 BPM. In some embodiments, the NSVT time duration may be between 5 seconds and 15 seconds. In some embodiments, a series of detected QRS signals may have a similar calculated QRS morphology. The QRS morphology similarity may be calculated using the feature correlation coefficient of at least two incoming sequential QRS complexes. In some embodiments, a series of detected QRS signals may have a dissimilar normal sinus rhythm (NSR) morphology.

In some embodiments, the NSVT episode may satisfy an R-R stability criterion. The R-R stability criterion may be satisfied when a difference between at least two consecutive R-R intervals is approximately less than 20 milliseconds. In some embodiments, the method may store the episode of NSVT based at least in part on the diagnosing.

In another embodiment, a WCD is described. The WCD includes a support structure wearable by a person, a processor coupled to the support structure, and a discharge circuit configured to discharge a stored electrical charge through a body of the patient. The discharge circuit is in communication with the processor. The processor configured to process at least one electrocardiogram (ECG) signal and diagnose an episode of nonsustained ventricular tachycardia (NSVT) based at least in part on the processing of the at least one ECG signal.

In some embodiments, the NSVT episode may satisfy an NSVT time duration and a QRS criterion. The NSVT time duration may be between 5 seconds and 15 seconds. In some instances, the QRS criterion may be a temporary QRS template of two sequential incoming QRS complexes. In some embodiments, the processor may determine a similarity between the temporary QRS template and at least two subsequent QRS complexes by calculating a feature correlation coefficient between the QRS template and the subsequent QRS complexes.

In some embodiments, the NSVT episode may exceed a heart rate threshold and an NSVT time threshold. The heart rate threshold may be 170 BPM. In some embodiments, the NSVT time duration may be between 5 seconds and 15 seconds. In some embodiments, a series of detected QRS signals may have a similar calculated QRS morphology. The QRS morphology similarity may be calculated using the feature correlation coefficient of at least two incoming sequential QRS complexes. In some embodiments, a series of detected QRS signals may have a dissimilar normal sinus rhythm (NSR) morphology.

In some embodiments, the NSVT episode may satisfy an R-R stability criterion. The R-R stability criterion may be satisfied when a difference between at least two consecutive R-R intervals is approximately less than 20 milliseconds. In some embodiments, the processor may store the episode of NSVT based at least in part on the diagnosing.

In another embodiment, a method to monitor a heart of a patient is described. The method processes at least one electrocardiogram (ECG) signal and generates a temporary QRS template of sequential incoming QRS complexes from the ECG signal. The method then determines a similarity between the temporary QRS template and subsequent QRS complexes by calculating a feature correlation coefficient between the QRS template and the subsequent QRS complexes. The method categorizes an episode of potential nonsustained ventricular tachycardia (NSVT) based at least in part on the similarity between the temporary QRS template and the at least two subsequent QRS complexes and stores the episode of potential NSVT based at least in part on the categorizing.

BRIEF DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein.

DETAILED DESCRIPTION

Figure 1:
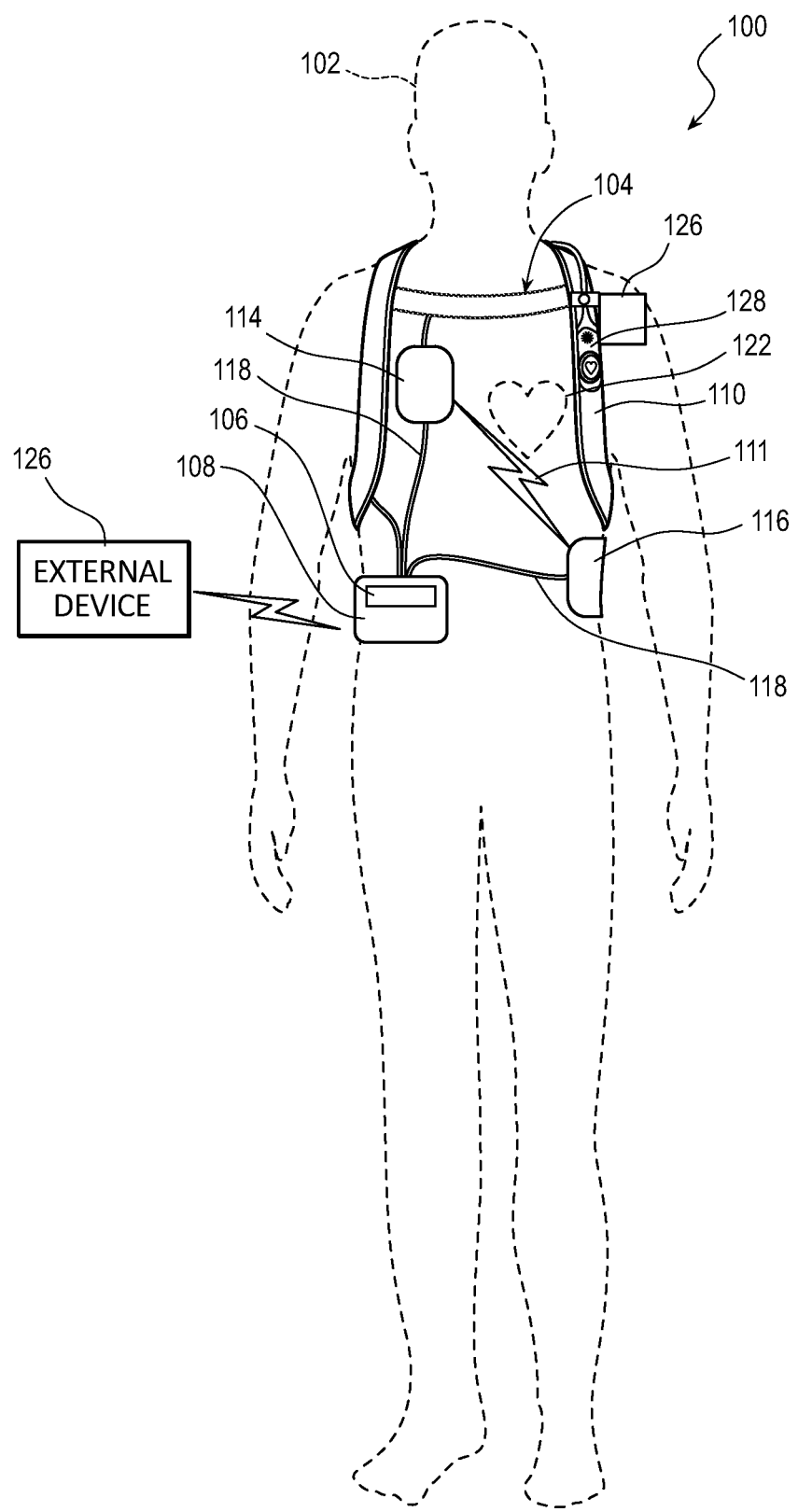
FIG. 1 is a diagram of a sample WCD system in accordance with exemplary embodiments described herein.

The detailed description set forth below in connection with the appended drawings, where like numerals reference like elements, are intended as a description of various embodiments of the present disclosure and are not intended to represent the only embodiments. Each embodiment described in this disclosure is provided merely as an example or illustration and should not be construed as precluding other embodiments. The illustrative examples provided herein are not intended to be exhaustive or to limit the disclosure to the precise forms disclosed.

In the following description, specific details are set forth to provide a thorough understanding of exemplary embodiments of the present disclosure. It will be apparent to one skilled in the art, however, that the embodiments disclosed herein may be practiced without embodying all of the specific details. In some instances, well-known process steps have not been described in detail in order not to unnecessarily obscure various aspects of the present disclosure. Further, it will be appreciated that embodiments of the present disclosure may employ any combination of features described herein.

Wearable Cardioverter Defibrillators (WCDs) are worn by patients at risk for sudden cardiac arrest and other potential heart conditions. Some patients may be at risk to develop sustained ventricular arrhythmias and sudden death. Non-sustained ventricular tachycardia (NSVT) is usually asymptomatic and most often diagnosed during cardiac monitoring; NSVT is also a potential marker for the development of sustained ventricular arrhythmias. NSVT may occur frequently while a patient is sleeping and the WCD system, or other heart rate monitoring system, may not detect or recognize the presence of NSVT.

In some instances, sensors signals may experience artifacts from patient motion or from the environment, as WCD patients are often conscious, ambulatory people living normal lives. Therefore, a short NSVT is not typically recognized and stored for later review because artifacts may cause too many short-lived high-rate signal rhythms. The disclosure herein describes a method to detect NSVT and store the ECG signals for clinical review and optimal patient management.

Morphology information may screen noise episodes out from real episodes of NSVT. If detected QRS complexes have a consistent morphology, or shape, then the signal likely does not contain much noise. Noise would make the complexes appear different or varied. Episode determination becomes more specific by factoring morphology. The specific factoring may identify shorter runs of VT, or if longer durations are allowed, episodes could be opened with greater confidence of avoiding noise. Using consistent morphology as a factor in episode determination can also be used to store monomorphic VT episodes as well as SVT episodes. Monomorphic VT episodes typically have a greater QRS width than SVT episodes.

For exemplary purposes only, the embodiments herein will be described in reference to a WCD system and a defibrillator. However, the methodology for detecting and storing an NSVT episode can be performed by a WCD or any wearable medical monitoring device that monitors a patient's ECG.

FIG. 1 illustrates a system 100 with a patient 102 wearing an example of a WCD system 104 according to embodiments described herein. In some embodiments, the WCD system 104 may include one or more communication devices 106, a support structure 110, and an external defibrillator 108 connected to two or more defibrillation electrodes 114, 116, among other components.

The support structure 110 may be worn by the patient 102. The patient 102 may be ambulatory, meaning the patient 102 can walk around and is not necessarily bed-ridden while wearing the wearable portion of the WCD system 104. While the patient 102 may be considered a "user" of the WCD system 104, this is not a requirement. For instance, a user of the WCD system 104 may also be a clinician such as a doctor, nurse, emergency medical technician (EMT) or other similarly tasked individual or group of individuals. In some cases, a user may even be a bystander. The particular context of these and other related terms within this description should be interpreted accordingly.

In some embodiments, the support structure 110 may include a vest, shirt, series of straps, or other system enabling the patient 102 to carry at least a portion of the WCD system 104 on the patient's body. In some embodiments, the support structure 110 may comprise a single component. For example, the support structure 110 may comprise a vest or shirt that properly locates the WCD system 104 on a torso 112 of the patient 102. The single component of the support structure 110 may additionally carry or couple to all of the various components of the WCD system 104.

In other embodiments, the support structure 110 may comprise multiple components. For example, the support structure 110 may include a first component resting on a patient's shoulders. The first component may properly locate a series of defibrillation electrodes 114, 116 on the torso 112 of the patient 102. A second component may rest more towards a patient's hips, whereby the second component may be positioned such that the patient's hips support the heavier components of the WCD system 104. In some embodiments, the heavier components of the WCD system 104 may be carried via a shoulder strap or may be kept close to the patient 102 such as in a cart, bag, stroller, wheelchair, or other vehicle.

The external defibrillator 108 may be coupled to the support structure 110 or may be carried remotely from the patient 102. The external defibrillator 108 may be triggered to deliver an electric shock to the patient 102 when patient 102 wears the WCD system 104. For example, if certain thresholds are exceeded or met, the external defibrillator 108 may engage and deliver a shock to the patient 102.

The defibrillation electrodes 114, 116 can be configured to be worn by patient 102 in a number of ways. For instance, the defibrillator 108 and the defibrillation electrodes 114, 116 can be coupled to the support structure 110 directly or indirectly. For example, the support structure 110 can be configured to be worn by the patient 102 to maintain at least one of the electrodes 114, 116 on the body of the patient 102, while the patient 102 is moving around, etc. The electrodes 114, 116 can be thus maintained on the torso 112 by being attached to the skin of patient 102, simply pressed against the skin directly or through garments, etc. In some embodiments, the electrodes 114, 116 are not necessarily pressed against the skin but becomes biased that way upon sensing a condition that could merit intervention by the WCD system 104. In addition, many of the components of defibrillator 108 can be considered coupled to support structure 110 directly, or indirectly via at least one of defibrillation electrodes 114, 116.

The WCD system 104 may defibrillate the patient 102 by delivering an electrical charge, pulse, or shock 111 to the patient 102 through a series of electrodes 114, 116 positioned on the torso 112. For example, when defibrillation electrodes 114, 116 are in good electrical contact with the torso 112 of patient 102, the defibrillator 108 can administer, via electrodes 114, 116, a brief, strong electric pulse 111 through the body. The pulse 111 is also known as shock, defibrillation shock, therapy, electrotherapy, therapy shock, etc. The pulse 111 is intended to go through and restart heart 122, in an effort to save the life of patient 102. The pulse 111 can further include one or more pacing pulses of lesser magnitude to pace heart 122 if needed. The electrodes 114, 116 may be electrically coupled to the external defibrillator 108 via a series of electrode leads 118. The defibrillator 108 may administer an electric shock 111 to the body of the patient 102 when the defibrillation electrodes 114, 116 are in good electrical contact with the torso 112 of patient 102. In some embodiments, devices (not shown) proximate the electrodes 114, 116 may emit a conductive fluid to encourage electrical contact between the patient 102 and the electrodes 114, 116.

In some embodiments, the WCD system 104 may also include either an external or internal monitoring device or some combination thereof. FIG. 1 displays an external monitoring device 124 which may also be known as an outside monitoring device. The monitoring device 124 may monitor at least one local parameter. Local parameters may include a physical state of the patient 102 such as ECG, movement, heartrate, pulse, temperature, and the like. Local parameters may also include a parameter of the WCD 104, environmental parameters, or the like. The monitoring device 124 may be physically coupled to the support structure 110 or may be proximate the support structure 110. In either location, the monitoring device 124 is communicatively coupled with other components of the WCD 104.

For some of these parameters, the device 124 may include one or more sensors or transducers. Each one of such sensors can be configured to sense a parameter of the patient 102, and to render an input responsive to the sensed parameter. In some embodiments, the input is quantitative, such as values of a sensed parameter; in other embodiments, the input is qualitative, such as informing whether or not a threshold is crossed. In some instances, these inputs about the patient 102 are also referred to herein as patient physiological inputs and patient inputs. In some embodiments, a sensor can be construed more broadly, as encompassing many individual sensors.

In some embodiments, a communication device 106 may enable the patient 102 to interact with, and garnish data from, the WCD system 104. The communication device 106 may enable a patient or third party to view patient data, dismiss a shock if the patient is still conscious, turn off an alarm, and otherwise engage with the WCD system 104. In some embodiments, the communication device 106 may be a separable part of an external defibrillator 108. For example, the communication device 106 may be a separate device coupled to the external defibrillator 108. In some embodiments, the communication device 106 may be wired or wirelessly linked to the external defibrillator 108 and may be removable from the defibrillator 108. In other embodiments, the communication device 106 may form an inseparable assembly and share internal components with the external defibrillator 108. In some embodiments, the WCD system 104 may include more than one communication device 106. For example, the defibrillator 108 may include components able to communicate to the patient and the WCD system 104 may include a separate communication device 106 remote form the defibrillator 108.

In some embodiments, the communication device 106 may be communicatively coupled to an alert button 128. The alert button 128 may be removably coupled to the support structure 110. The patient 102 may couple the alert button 128 to the support structure 110 or may couple the alert button 128 to an article of clothing. The alert button 128 may have wired or wireless connection to the communication device 106. In some embodiments, the alert button 128 may include a visual output, an audio output, and a user input. The visual output may include a light, such as an LED, a small screen, or some combination thereof. Likewise, the audio output may include one or more speakers. The output of the audio output may be loud enough to be heard over nominal background noise. In some embodiments, the audio output might have an adjustable volume range. In some embodiments, the alert button 128 may include a microphone. In still further embodiments, the alert button 128 may also include a haptic response.

In some embodiments, the defibrillator 108 may connect with one or more external devices 126. For example, as shown in FIG. 1, the defibrillator 108 may connect to various external devices 126 such as the cloud, a remote desktop, a laptop, a mobile device, or other external device using a network such as the Internet, local area networks, wide area networks, virtual private networks (VPN), other communication networks or channels, or any combination thereof.

In embodiments, one or more of the components of the exemplary WCD system 104 may be customized for the patient 102. Customization may include a number of aspects including, but not limited to, fitting the support structure 110 to the torso 112 of patient 102; baseline physiological parameters of patient 102 can be measured, such as the heart rate of patient 102 while resting, while walking, motion detector outputs while walking, etc. The measured values of such baseline physiological parameters can be used to customize the WCD system, in order to make its diagnoses more accurate, since patients' bodies differ from one another. Of course, such parameter values can be stored in a memory of the WCD system, and the like. Moreover, a programming interface can be made according to embodiments, which receives such measured values of baseline physiological parameters. Such a programming interface may input automatically in the WCD system these, along with other data.

Figure 2:
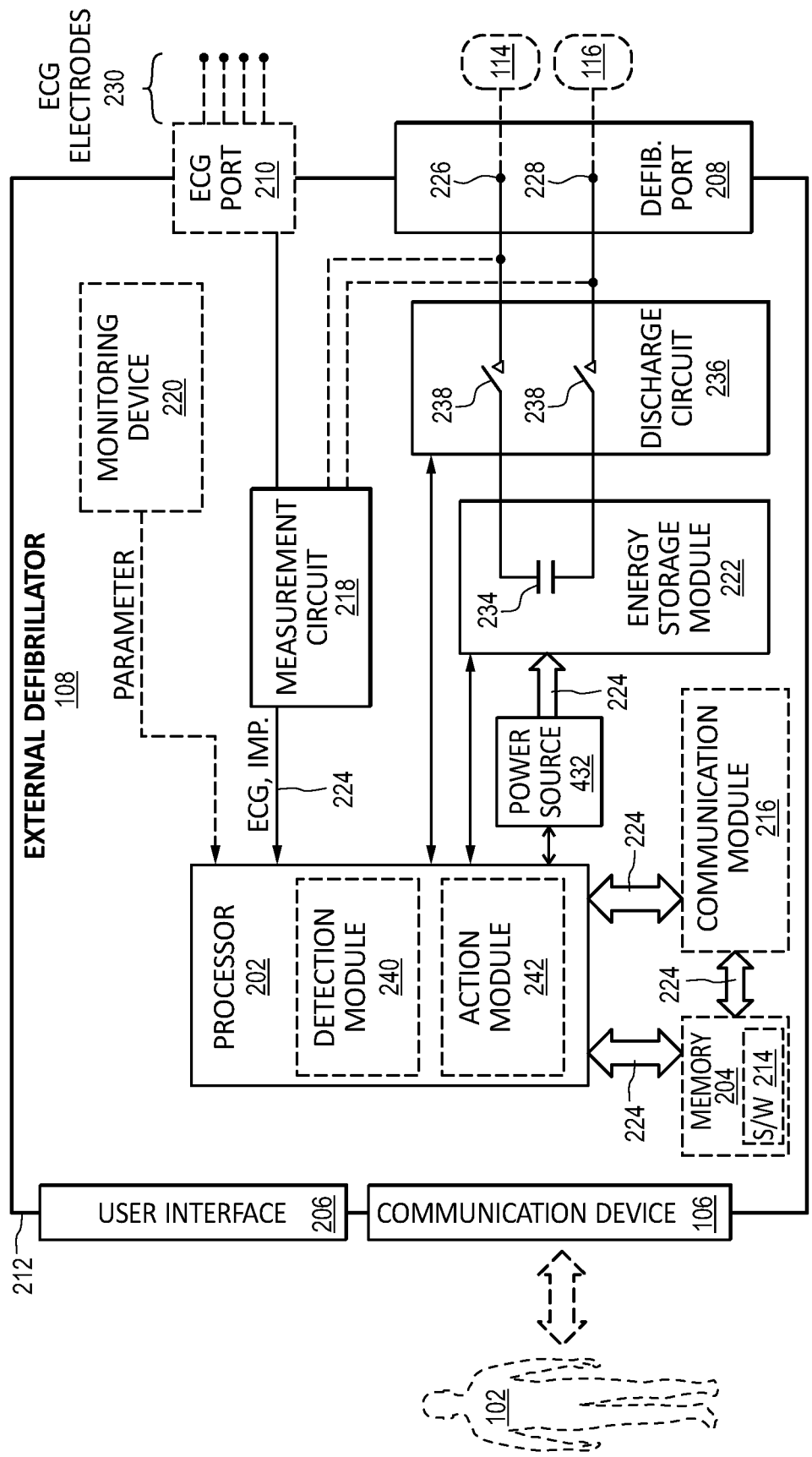
FIG. 2 is a block diagram of an example defibrillator in accordance with exemplary embodiments described herein.

FIG. 2 is a diagram displaying various components of an example external defibrillator 108. The external defibrillator 108 may be an example of the defibrillator 108 described with reference to FIG. 1. The components shown in FIG. 2 may be contained within a single unit or may be separated amongst two or more units in communication with each other. The defibrillator 108 may include a communication device 106, processor 202, memory 204, defibrillation port 208, and ECG port 210, among other components. In some embodiments, the components are contained within a housing 212 or casing. The housing 212 may comprise a hard shell around the components or may comprise a softer shell for increased patient comfort.

The communication device 106, processor 202, memory 204 (including software/firmware code (SW) 214), defibrillation port 208, ECG port 210, communication module 216, measurement circuit 218, monitoring device 220, and energy storage module 222 may communicate, directly or indirectly, with one another via one or more buses 224. The one or more buses 224 may allow data communication between the elements and/or modules of the defibrillator 108.

The memory 204 may include random access memory (RAM), read only memory (ROM), flash RAM, and/or other types. The memory 204 may store computer-readable, computer-executable software/firmware code 214 including instructions that, when executed, cause the processor 202 to perform various functions (e.g., determine shock criteria, determine consciousness of patient, track patient parameters, establish electrode channels, determine noise levels in electrode readings, etc.). In some embodiments, the processor 202 may include an intelligent hardware device, e.g., a central processing unit (CPU), a microcontroller, an application-specific integrated circuit (ASIC), etc.

In some embodiments, the memory 204 can contain, among other things, the Basic Input-Output system (BIOS) which may control basic hardware and/or software operations such interactions and workings of the various components of the defibrillator 108, and in some embodiments, components external to the defibrillator 108. For example, the memory 204 may contain various modules to implement the workings of the defibrillator 108 and other aspects of the present disclosure.

In some embodiments, the defibrillator 108 may include a user interface 206. The user interface 406 may be in addition to or part of the communication device 106. The user interface 406 may display an ECG of the patient, a status of the defibrillator 108, a status of a charge (e.g., a battery charge or an energy storage module), and the like.

In some embodiments, the defibrillator 108 may include a defibrillation port 208. The defibrillation port 208 may comprise a socket, opening, or electrical connection in the housing 212. In some instances, the defibrillation port 208 may include two or more nodes 226, 228. The two or more nodes 226, 228 may accept two or more defibrillation electrodes (e.g., defibrillation electrodes 114, 116, FIG. 1). The nodes 226, 228 may provide an electrical connection between the defibrillation electrodes 114, 116 and the defibrillator 108. The defibrillation electrodes 114, 116 may plug into the two or more nodes 226, 228 via one or more leads (e.g., leads 118), or, in some instances, the defibrillation electrodes 114, 116 may be hardwired to the nodes 226, 228. Once an electrical connection is established between the defibrillation port 208 and the electrodes 114, 116, the defibrillator 108 may be able to deliver an electric shock to the patient 102.

In some embodiments, the defibrillator 108 may include an ECG port 210 in the housing 212. The ECG port 210 may accept one or more ECG electrodes 230 or ECG leads. In some instances, the ECG electrodes 230 sense a patient's ECG signal. For example, the ECG electrodes 230 may record electrical activity generated by heart muscle depolarization. The ECG electrodes 230 may utilize 4-leads to 12-leads or multichannel ECG, or the like. The ECG electrodes 230 may connect with the patient's skin.

In some embodiments, the defibrillator 108 may include a measurement circuit 218. The measurement circuit 218 may be in communication with the ECG port 210. For example, the measurement circuit 218 may receive physiological signals from ECG port 210. The measurement circuit 218 may additionally or alternatively receive physiological signals via the defibrillation port 208 when defibrillation electrodes 114, 116 are attached to the patient 102. The measurement circuit 218 may determine a patient's ECG signal from a difference in voltage between the defibrillation electrodes 114, 116.

In some embodiments, the measurement circuit 218 may monitor the electrical connection between the defibrillation electrodes 114, 116 and the skin of the patient 102. For example, the measurement circuit 218 can detect impedance between electrodes 114, 116. The impedance may indicate the effective resistance of an electric circuit. An impedance calculation may determine when the electrodes 114, 116 have a good electrical connection with the patient's body.

In some embodiments, the defibrillator 108 may include an internal monitoring device 220 within the housing 212. The monitoring device 220 may monitor at least one local parameter. Local parameters may include physical state of the patient such as ECG, movement, heartrate, pulse, temperature, and the like. Local parameters may also include a parameter of the WCD system (e.g., WCD 104, FIG. 1), defibrillator 108, environmental parameters, or the like.

In some embodiments, the WCD system 104 may include an internal monitoring device 220 and an external monitoring device (e.g., external monitoring device 124). If both monitoring devices 124, 220 are present, the monitoring devices 124, 220 may work together to parse out specific parameters depending on position, location, and other factors. For example, the external monitoring device 124 may monitor environmental parameters while the internal monitoring device 220 may monitor patient and system parameters.

In some embodiments, the defibrillator 108 may include a power source 232. The power source 232 may comprise a battery or battery pack, which may be rechargeable. In some instances, the power source 232 may comprise a series of different batteries to ensure the defibrillator 108 has power. For example, the power source 232 may include a series of rechargeable batteries as a prime power source and a series of non-rechargeable batteries as a secondary source. If the patient 102 is proximate an AC power source, such as when sitting down, sleeping, or the like, the power source 232 may include an AC override wherein the power source 232 draws power from the AC source.

In some embodiments, the defibrillator 108 may include an energy storage module 222. The energy storage module 222 may store electrical energy in preparation or anticipation of providing a sudden discharge of electrical energy to the patient. In some embodiments, the energy storage module 222 may have its own power source and/or battery pack. In other embodiments, the energy storage module 222 may pull power from the power source 232. In still further embodiments, the energy storage module 222 may include one or more capacitors 234. The one or more capacitors 234 may store an electrical charge, which may be administered to the patient. The processor 202 may be communicatively coupled to the energy storage module 222 to trigger the amount and timing of electrical energy to provide to the defibrillation port 208 and, subsequently, the patient 102.

In some embodiments, the defibrillator 108 may include a discharge circuit 236. The discharge circuit 236 may control the energy stored in the energy storage module 222. For example, the discharge circuit 236 may either electrical couple or decouple the energy storage module 222 to the defibrillation port 208. The discharge circuit 236 may be communicatively coupled to the processor 202 to control when the energy storage module 222 and the defibrillation port 208 should or should not be coupled to either administer or prevent a charge from emitting from the defibrillator 108. In some embodiments, the discharge circuit 236 may include on or more switches 238. In further embodiments, the one or more switches 238 may include an H-bridge.

In some embodiments, the defibrillator 108 may include a communication module 216. The communication module 216 may establish one or more communication links with either local hardware and/or software to the WCD system 104 and defibrillator 108 or to remote hardwire separate from the WCD system 104. In some embodiments, the communication module 216 may include one or more antennas, processors, and the like. The communication module 216 may communicate wirelessly via radio frequency, electromagnetics, local area networks (LAN), wide area networks (WAN), virtual private networks (VPN), RFID, Bluetooth, cellular networks, and the like. The communication module 216 may facilitate communication of data and commands such as patient data, episode information, therapy attempted, CPR performance, system data, environmental data, and so on.

In some embodiments, the processor 202 may execute one or more modules. For example, the processor 202 may execute a detection module 240 and/or an action module 242. The detection module 240 may be a logic device or algorithm to determine if any or a variety of thresholds are exceeded which may require action of the defibrillator 108. For example, the detection module 240 may receive and interpret all of the signals from the ECG port 210, the defibrillation port 208, the monitoring device 220, an external monitoring device, and the like. The detection module 240 may process the information to ensure the patient is still conscious and healthy. If any parameter indicates the patient 102 may be experiencing distress or indicating a cardiac episode, the detection module 240 may activate the action module 242.

The action module 242 may receive data from the detection module 240 and perform a series of actions. For example, an episode may merely be a loss of batter power at the power source 232 or the energy storage module 222, or one or more electrodes (e.g., ECG electrodes, defibrillation electrodes) may have lost connection. In such instances, the action module 242 may trigger an alert to the patient or to an outside source of the present situation. This may include activating an alert module. If an episode is a health risk, such as a cardiac event, the action module 242 may begin a series of steps. This may include issuing a warning to the patient, issuing a warning to a third party, priming the energy storage module 222 for defibrillation, releasing one or more conductive fluids proximate defibrillation electrodes 114, 116, and the like.

Figure 3:
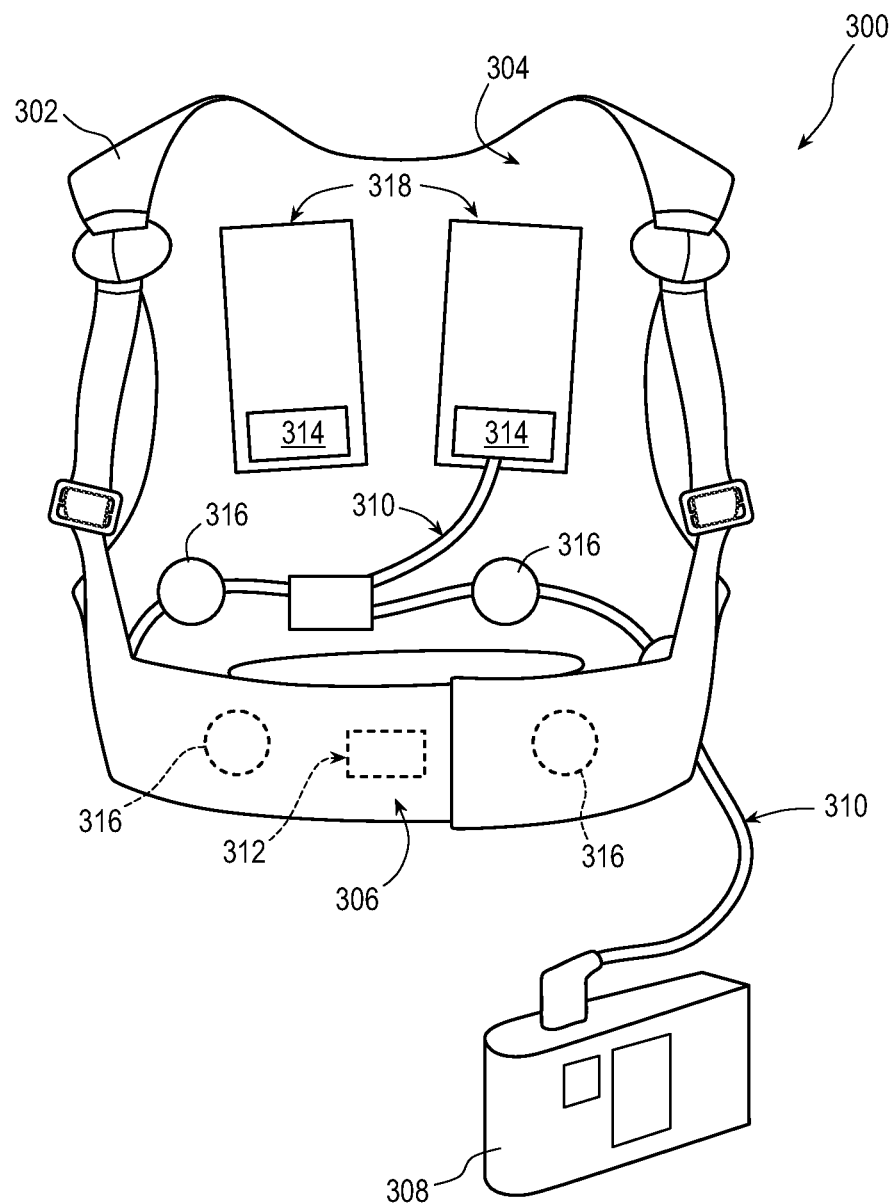
FIG. 3 is a diagram of sample embodiments of components of a WCD system in accordance with exemplary embodiments described herein.

FIG. 3 is a diagram of sample embodiments of components of a WCD system 300 according to exemplary embodiments. The WCD system 300 may be an example of the WCD system 104 describe with reference to FIG. 1. In some embodiments, the WCD system 300 may include a support structure 302 comprising a vest-like wearable garment. In some embodiments, the support structure 302 has a back side 304, and a front side 306 that closes in front of the chest of the patient.

In some embodiments, the WCD system 300 may also include an external defibrillator 308. The external defibrillator 308 may be an example of the defibrillator 108 describe with reference to FIGS. 1 and 2. As illustrated, FIG. 3 does not show any support for the external defibrillator 308, but as discussed, the defibrillator 308 may be carried in a purse, on a belt, by a strap over the shoulder, and the like as discussed previously. One or more wires 310 may connect the external defibrillator 308 to one or more electrodes 312, 314, 316. Of the connected electrodes, electrodes 312, 314 are defibrillation electrodes, and electrodes 316 are ECG sensing electrodes.

The support structure 302 is worn by the patient to maintain electrodes 312, 314, 316 on a body of the patient. For example, the back-defibrillation electrodes 314 are maintained in pockets 318. In some embodiments, the inside of pockets 318 may comprise loose netting, so that the electrodes 314 can contact the back of the patient. In some instances, a conductive fluid may be deployed to increase connectivity. Additionally, in some embodiments, sensing electrodes 316 are maintained in positions that surround the patient's torso, for sensing ECG signals and/or the impedance of the patient.

In some instances, the ECG signals in a WCD system 300 may comprise too much electrical noise to be useful. To ameliorate the problem, multiple ECG sensing electrodes 316 are provided, for presenting many options to the processor (202. The multiple ECG sensing electrodes 316 provide different vectors for sensing the ECG signal of the patient.

Figure 4:
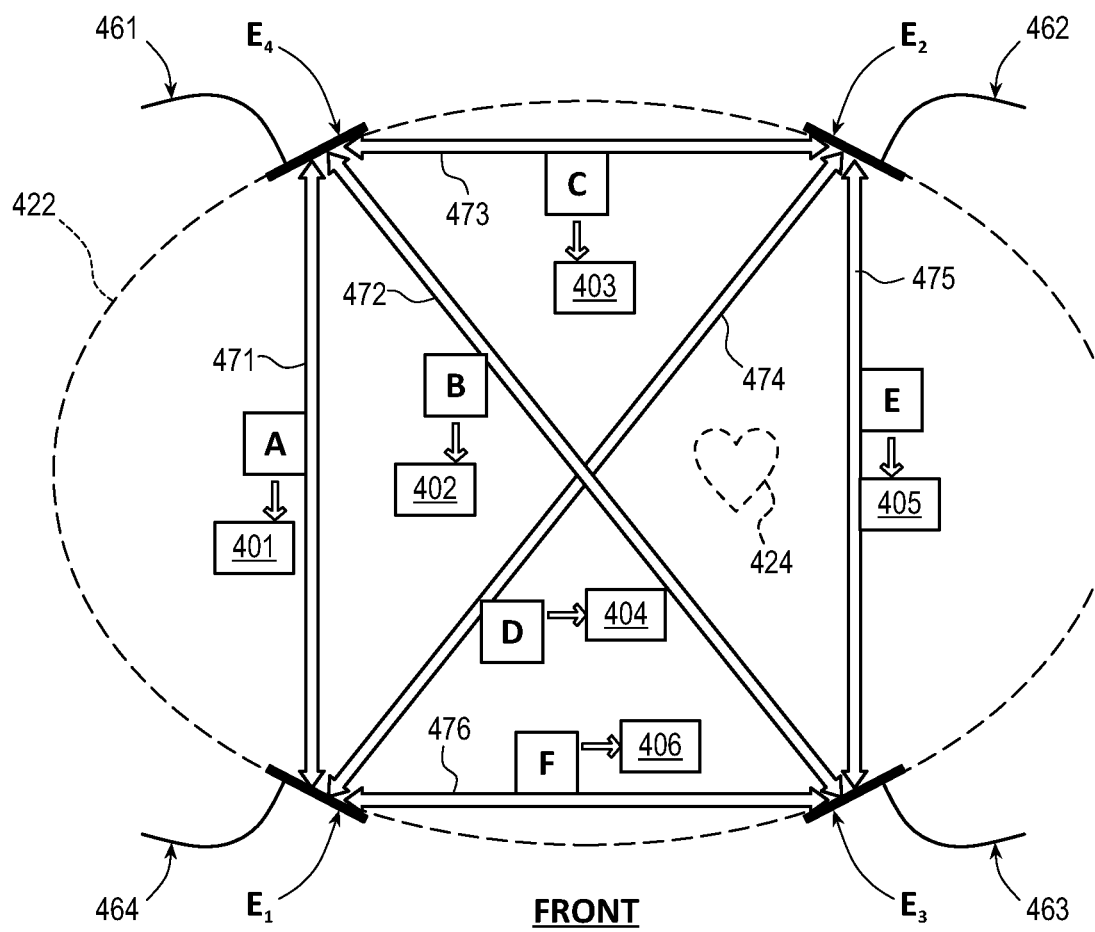
FIG. 4 is a conceptual diagram illustrating multiple electrodes of a WCD system in accordance with exemplary embodiments described herein.

FIG. 4 is a conceptual diagram illustrating how multiple electrodes of a WCD system may defined a multi-vector embodiment for sensing ECG signals along different vectors according to various exemplary embodiments. A cross-section of a body of a patient 422 having a heart 424 is illustrated. In FIG. 4, the patient 422 is viewed from the top looking down and the plane of FIG. 4 intersects patient 422 proximate the torso of the patient 422.

In some embodiments, four ECG sensing electrodes $E_1$, $E_2$, $E_3$, $E_4$ are maintained on the torso of patient 482, and have respective wire leads 461, 462, 463, 464. The electrodes $E_1$, $E_2$, $E_3$, $E_4$ that surround the torso may be similar to the sensing electrodes 316 as described with reference to FIG. 3.

Any pair of these four ECG sensing electrodes $E_1$, $E_2$, $E_3$, $E_4$ defines a vector, along which an ECG signal may be sensed and, in some instances, measured. As such, electrodes $E_1$, $E_2$, $E_3$, $E_4$ define six vectors 471, 472, 473, 474, 475, 476.

These vectors 471, 472, 473, 474, 475, 476 define channels A, B, C, D, E, F respectively. ECG signals 401, 402, 403, 404, 405, 406 may thus be sensed and/or measured from channels A, B, C, D, E, F, respectively, and in particular from the appropriate pairings of wire leads 461, 462, 463, 464 for each channel.

As shown FIG. 4, electrodes $E_1$, $E_2$, $E_3$, $E_4$ are drawn on the same plane for simplicity, while in actuality the electrodes $E_1$, $E_2$, $E_3$, $E_4$ may not be positioned on the same plane. Accordingly, vectors 471, 472, 473, 474, 475, 476 are not necessarily on the same plane, either. Further, in some embodiments, the WCD system averages a value of the voltages of all four electrodes electronically and then determines the voltage of each electrode relative to the average value. Conceptually, this average value is the signal at some point in space in between the electrodes $E_1$, $E_2$, $E_3$, $E_4$. It continuously changes its virtual position based on the voltages of the electrodes $E_1$, $E_2$, $E_3$, $E_4$. In some embodiments, this virtual point is referred to herein as the M Central Terminal (MCT). Relative to the MCT, there are four resulting vectors: E1C=E1−CM, E2C=E2−CM, E3C=E3−CM and E4C=E4−CM, where CM is the average voltage value. In some embodiments, the vectors are virtually formed by selecting a pair of these signals and subtracting one from the other. For example, E1C−E2C=(E1−CM)−(E2−CM)=E1−E2+(CM−CM)=E1−E2=E12. Although six vectors are described in FIG. 4, a different number of vectors may be used depending on the number of ECG electrodes present in the system and the desired number of vectors (up to the number of vectors that can be derived from the number of electrodes).

In some embodiments, to make the shock/no-shock determination as accurate as possible, a WCD system may assess the best ECG signals 401, 402, 403, 404, 405, 406 for rhythm analysis and interpretation. For example, ECG signals with the most noise may be ignored, discarded, or not considered, leaving the remaining ECG signals as candidates for the shock/no shock determination.

In other embodiments, the vectors may be aggregated to make a shock/no shock decision, and/or to determine the patient's heart rate and/or QRS widths. For example, in some embodiments the aggregation can be implemented as disclosed in U.S. Pat. No. 9,757,581 issued Sep. 12, 2017 entitled "WEARABLE CARDIOVERTER DEFIBRILLATOR COMPONENTS MAKING AGGREGATE SHOCK/NO SHOCK DETERMINATION FROM TWO OR MORE ECG SIGNALS," which is incorporated herein by reference.

Figure 5:
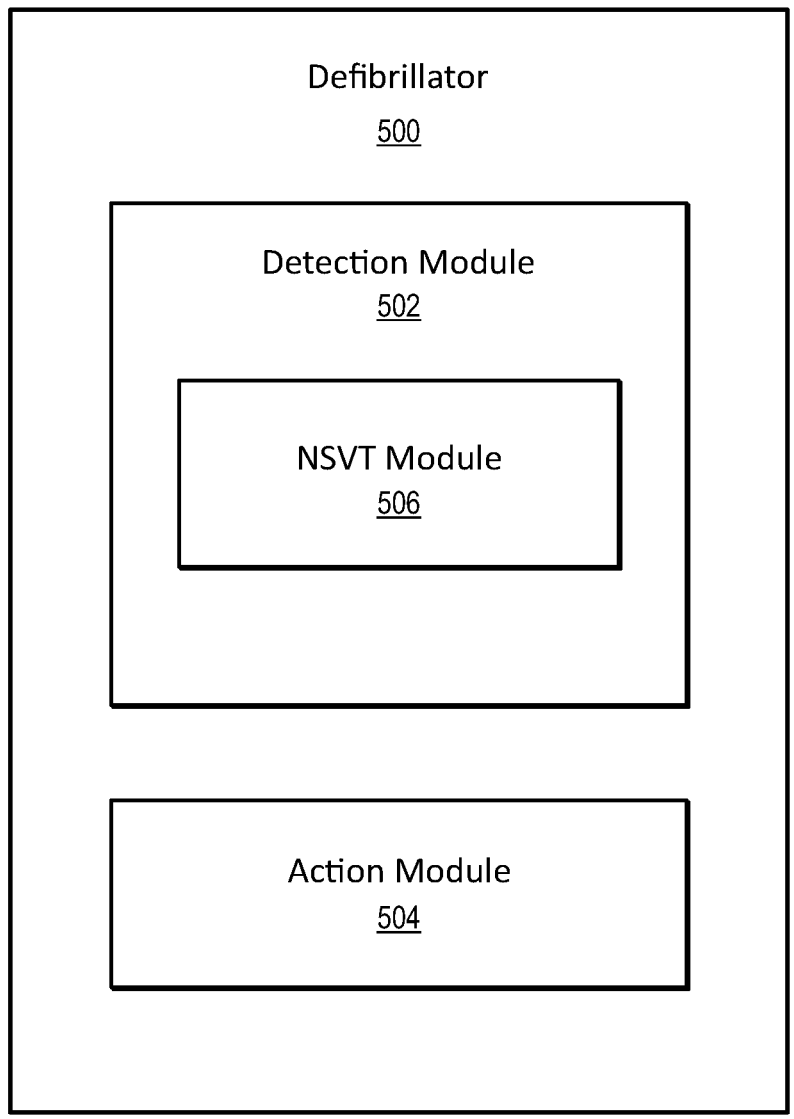
FIG. 5 is a is a block diagram of an example defibrillator in accordance with exemplary embodiments described herein.

FIG. 5 is a block diagram illustrating components of one example of a defibrillator 500. The defibrillator 500 may be an example of the defibrillator 108 described with reference to FIGS. 1 and 2 and defibrillator 308 described with reference to FIG. 3. In this example, the defibrillator 500 has detection module 502 and an alert module 504. The detection module 502 may further include an NSVT module 506.

In some embodiments, the NSVT module 506 may diagnose potential NSVT episodes and store episodic information for later review. For example, shorter runs of detected VT are analyzed to determine if there is a noisy signal. If there is noise in the signal, the episode is deemed a noise episode and is not saved. However, if the signal is validated, the NSVT module 506 flags a potential NSVT episode and the information is stored for later review.

In some embodiments, the NSVT module 506 may utilize morphonology information to ascertain the difference between noise and a potential cardiac event. Noisy signals typically have an erratic QRS complex as the noise in the signal affects the appearance of the complexes. However, QRS complexes with a consistent morphology or shape typically do not contain much noise. Using consistent morphology as a factor, the NSVT module 506 is able to more rigorously filter out potential cardiac episodes from noisy signals. The NSVT module 506 may open episodes for shorter VT occurrences, or if longer durations are allowed, the NSVT module 506 may open longer episodes with greater confidence of avoiding noise.

In some embodiments, the NSVT module 506 may also flag and store potential monomorphic VT episodes or SVT episodes. For some patients, monomorphic VT episodes may have a greater QRS width than SVT episodes, which the NSVT module 506 may factor into calculations. In some instances, a morphology analysis may screen out disorganized rhythms such as VF and polymorphic VT as potential NSVT but other portions of a shock decision algorithm may be used by the detection module 502 to detect and make a shock decision.

Figure 9:
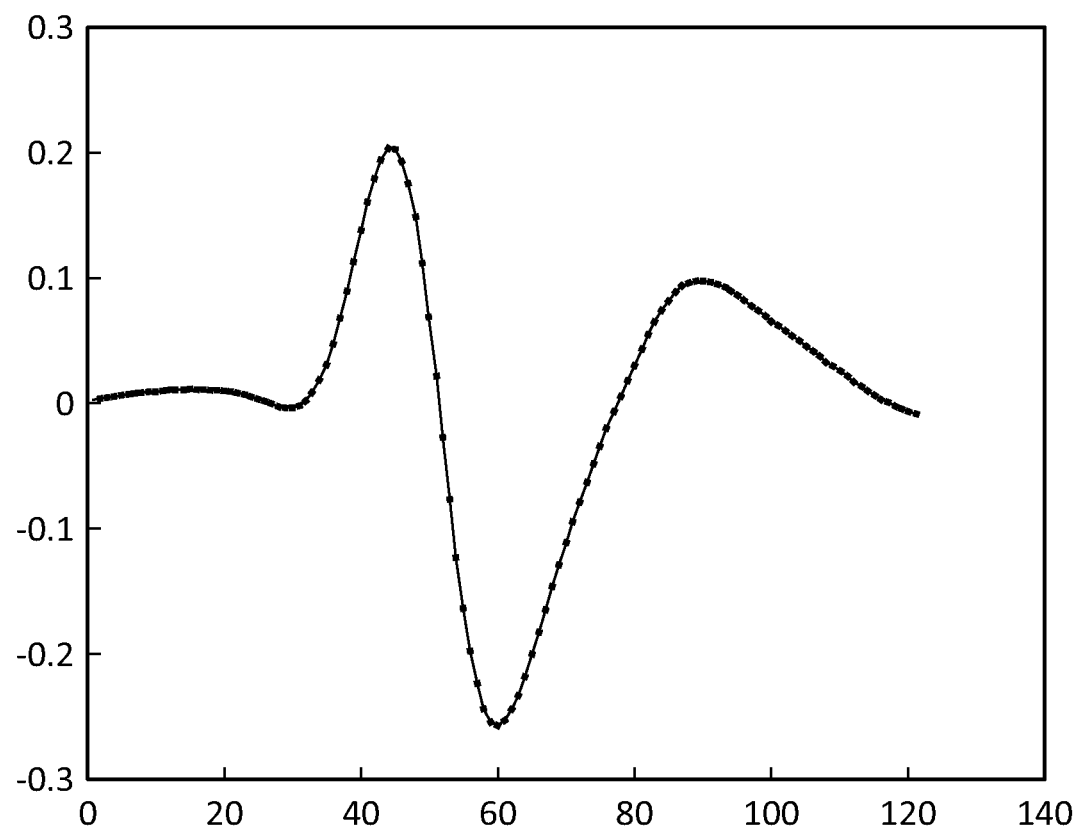
FIG. 9 is an exemplary NSR graphical representation in accordance with exemplary embodiments described herein.
Figure 10A:
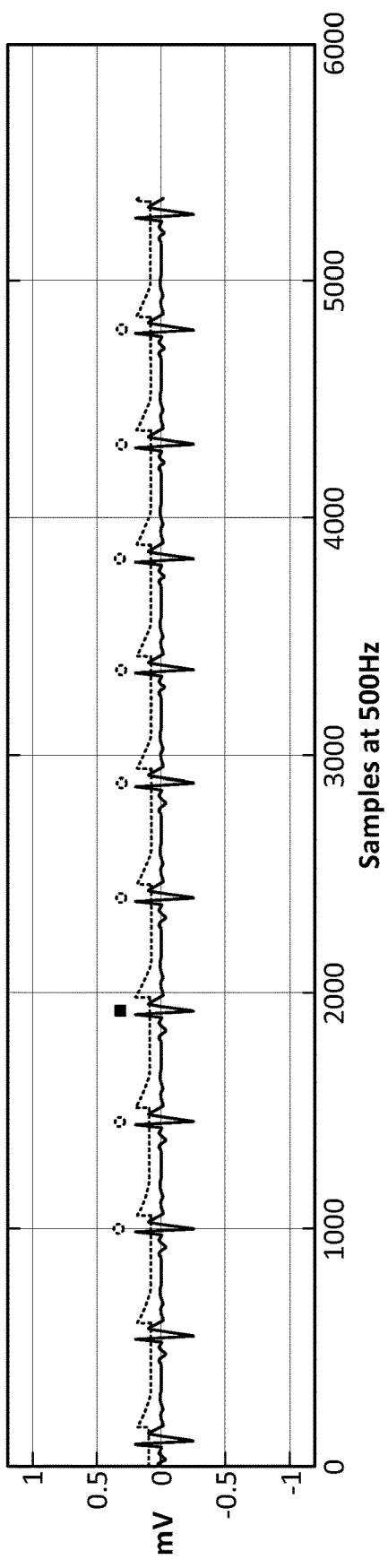
FIG. 10A illustrates an NSR heartrate graph in accordance with exemplary embodiments described herein.

In some embodiments, the NSVT module 506 may analyze QRS morphology by generating a QRS template. For example, during a normal rhythm, the NSVT module 506 may generate and store a template. FIG. 9 is an example of a normal template formed during normal sinus rhythm at a lower heartrate. FIG. 10A illustrates an NSR heartrate graph used to calculate the template in FIG. 9.

Referring back to FIG. 5, when a high or abnormal heartrate tachycardia begins, the NSVT module 506 may compare incoming QRS complexes to the QRS template. If the correlation is high, the NSVT module 506 may flag the incident as SVT. If the incoming QRS complexes have a low to zero correlation to the normal template but the QRS complexes are correlating to each other, the NSVT module 506 flags the episode as a potential NSVT episode.

In some embodiments, the NSVT module 506 may compare incoming QRS complexes by calculating a Feature Correlation Coefficient shown below:

$$FCC = \frac{\left(8\sum_{i=1}^{8} x_i y_i - \left(\sum_{i=1}^{8} x_i\right)\left(\sum_{i=1}^{8} y_i\right)\right)^2}{\left(8\sum_{i=1}^{8} x_i^2 - \left(\sum_{i=1}^{8} x_i\right)^2\right)\left(8\sum_{i=1}^{8} y_i^2 - \left(\sum_{i=1}^{8} y_i\right)^2\right)}$$

Figure 6:
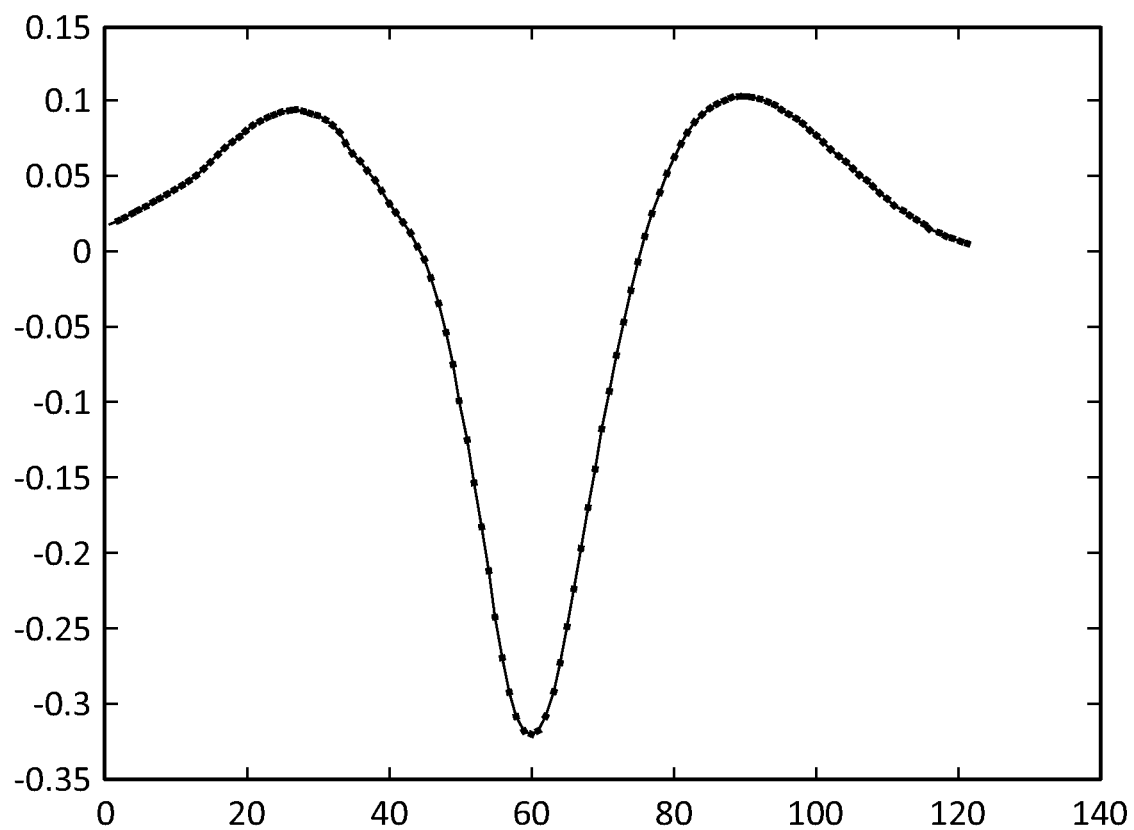
FIG. 6 illustrates an exemplary QRS template in accordance with exemplary embodiments described herein.
Figure 10B:
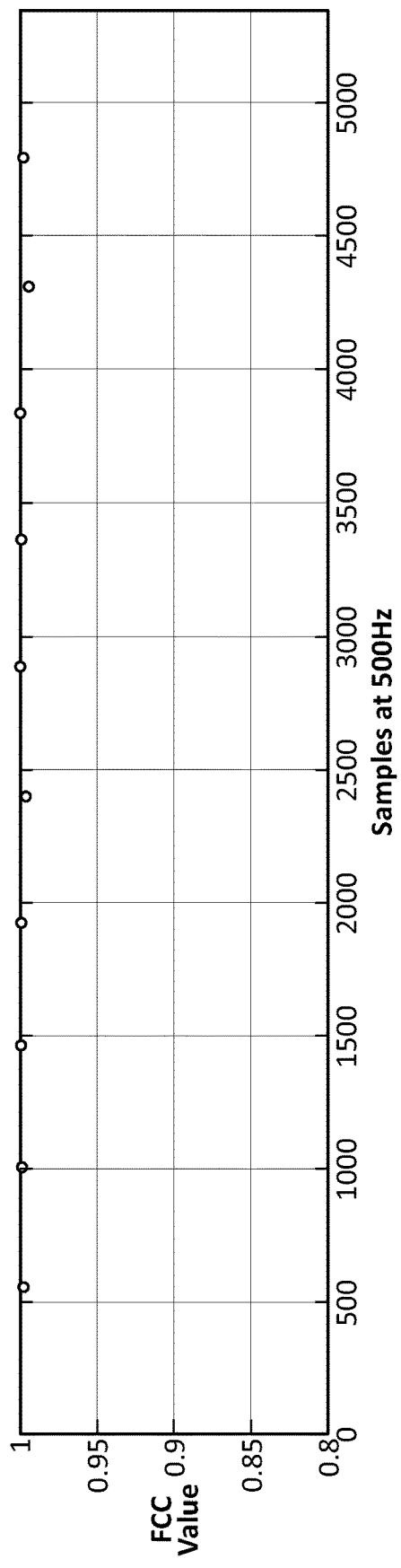
FIG. 10B illustrates a calculated FCC for the NSR heartrate graph of FIG. 10A in accordance with exemplary embodiments described herein.

The FCC may be calculated between two consecutive QRS complexes to determine the correlation. FIG. 10B shows the calculated FCC correlation for one example. In some embodiments, the NSVT module 506 may form a temporary NSVT template using the first few incoming QRS complexes and then calculate the FCC. As shown in FIG. 6, the temporary template may be formed as a median or mean value of multiple waveforms. The exemplary waveform shown in FIG. 6 is a template waveform from median values. In further embodiments, the FCC to a normal template may be low but consistent.

In other embodiments, another method of detecting morphology consistency uses the QRS organization metric described in U.S. patent application Ser. No. 16/554,410 filed Aug. 28, 2019 with a request for non-publication. In these embodiments, the organization metric of the '410 application is similar to the FCC except that it uses the sum of the squared difference between the template and the incoming signal. An organization value of two (2) or more indicates a very clean signal. VF and polymorphic VT is generally less than one (1).

Analyzing the QRS morphology may help in flagging potential NSVT or other non-sustained VT episodes. The QRS morphology allows the NSVT module 506 to determine if the ECG signal is clear and absent of any extra noise. If there is no noise in the system but the signal is showing signs of heart distress such as an accelerated heart rate, the NSVT module 506 may store the information for later review. Table 1, shown below, illustrates several factors for storing a potential NSVT episode. In some embodiments, the NSVT module 506 will store an episode when one of the listed conditions is satisfied. In further embodiments, the NSVT module 506 will store episodic information when at least two conditions are satisfied.

TABLE 1

Factors for Storing a Potential NSVT Episode

| Case | HR (bpm) | Sustained Duration | Similar Morphology | Similar to NSR Morphology | Stable to RR Intervals | Sudden Onset | Sleeping Posture |
|---|---|---|---|---|---|---|---|
| NSVT | >170 | >5 sec And <15 sec | Yes | No | Yes | Yes | Yes/No |

In some embodiments, the sleeping status of the patient is a factor in storing potential NSVT episode information. For example, a standard patient wearing a WCD is ambulatory and may ascertain when an NSVT episode is occurring when the patient is awake. However, if the patient is sleeping, the patient may not feel a VT or NSVT event. Therefore, in some embodiments, the NSVT module 506 may be programmed to truncate NSVT detection based on a waking status of the patient. For example, the NSVT module 506 may run when the patient is sleeping. Sleeping may be detected by the supine position, time, a slowing heartrate, and the like. In other embodiments, a doctor or clinician may not want to rely on the patient's ability to detect and record NSVT modules and may have the NSVT module 504 continuously monitoring the patient.

In some embodiments, the NSVT module 506 may screen episodes to differentiate between actual episodes and noise by factoring in the stability of the interval between QRS complexes. Noise generally causes false QRS detections, which creates heartrate variability, or R-R variability. R is a point corresponding to the peak of the QRS complex of the ECG wave, and R-R is an interval between success R points. R-R intervals are considered stable if the difference between two consecutive R-R-intervals is less than 20 milliseconds.

In some embodiments, the NSVT module 506 may detect and record a potential sudden onset. For example, a sudden onset may occur when the HR suddenly changes more than 10% and the morphology is not similar to the normal QRS template. The NSVT may categorize the morphology as similar if the FFC calculation is greater than 0.9. VT may start with a sudden increase of HR. Similarly, NSVT may start with a sudden HR increase, with a stable R-R interval and similar incoming QRS morphology. However, in contrast to SVT, NSVT has a different QRS morphology to when compared to the NSR template. In contrast, when a gradual HR increase is present, the patient is likely experiencing sinus tachycardia when exercising.

Figure 7A:
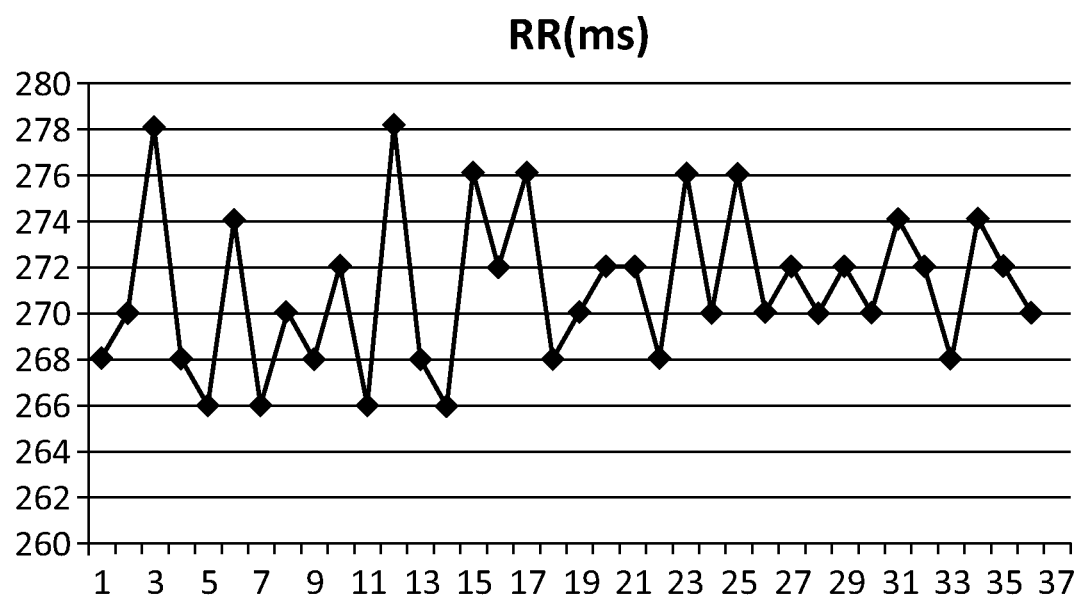
FIG. 7A illustrates exemplary R-R data in accordance with exemplary embodiments described herein.
Figure 7B:
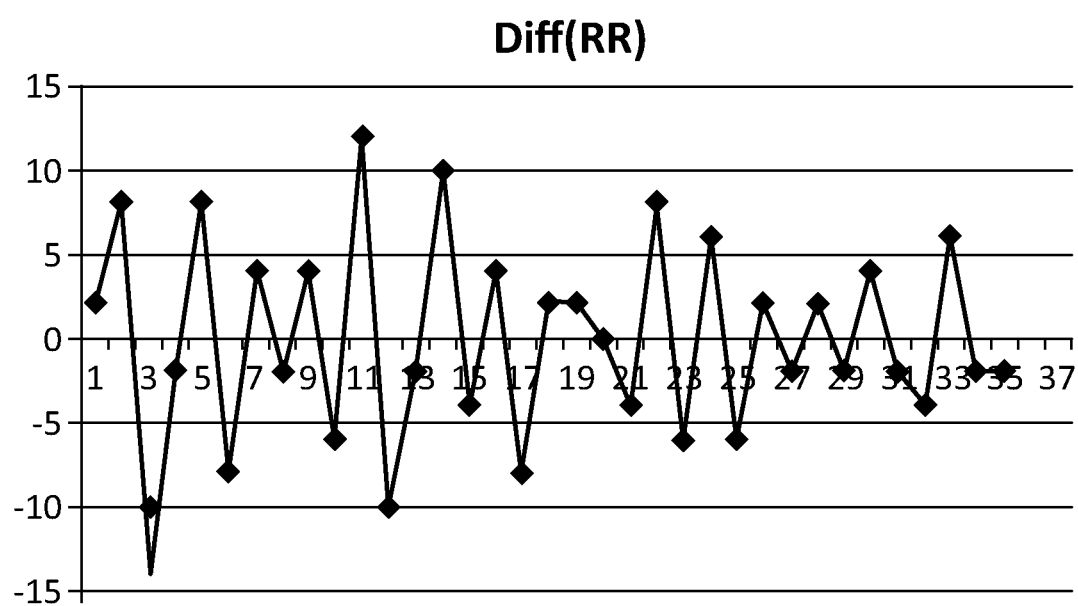
FIG. 7B illustrates exemplary R-R data in accordance with exemplary embodiments described herein.

FIGS. 7A and 7B is an embodiment of R-R analysis. In the example shown, FIG. 7A shows a patient with consistent R-R intervals. FIG. 7B shows the difference between the R-R intervals. FIG. 7B shows the difference between R-R intervals to be less than 20 milliseconds. Therefore, the example shown is a situation where the ECG signal is clear, and the patient may be experiencing an episode NSVT. A standard monitoring device might not view this as an interval and might dismiss the interval as noise. However, by reviewing the R-R intervals and consistency rating, the NSVT module 506 detects a potential NSVT episode and stores it for later review by physicians.

Figure 8A:
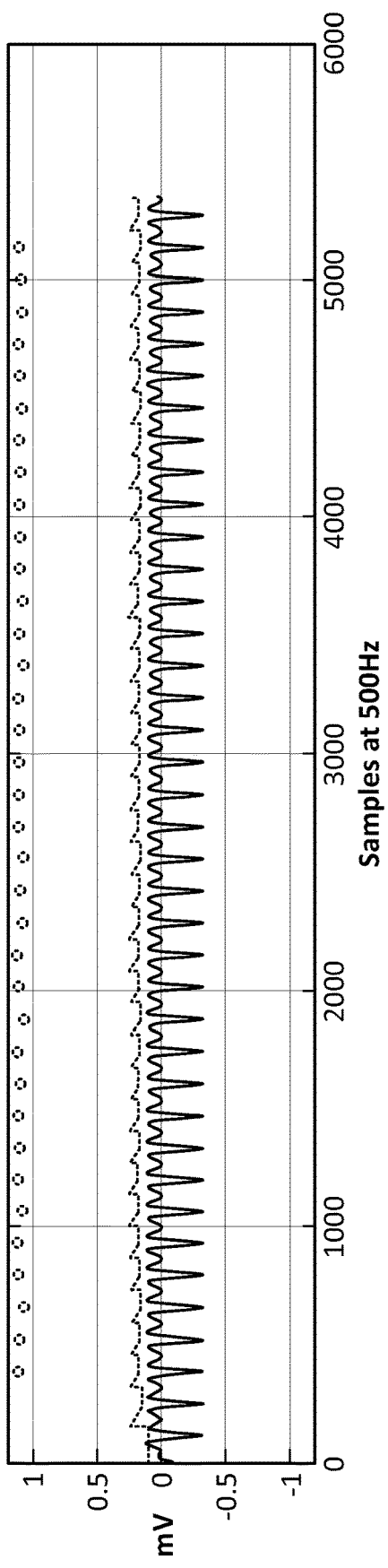
FIG. 8A illustrates an MVT heartrate graph in accordance with exemplary embodiments described herein.
Figure 8B:
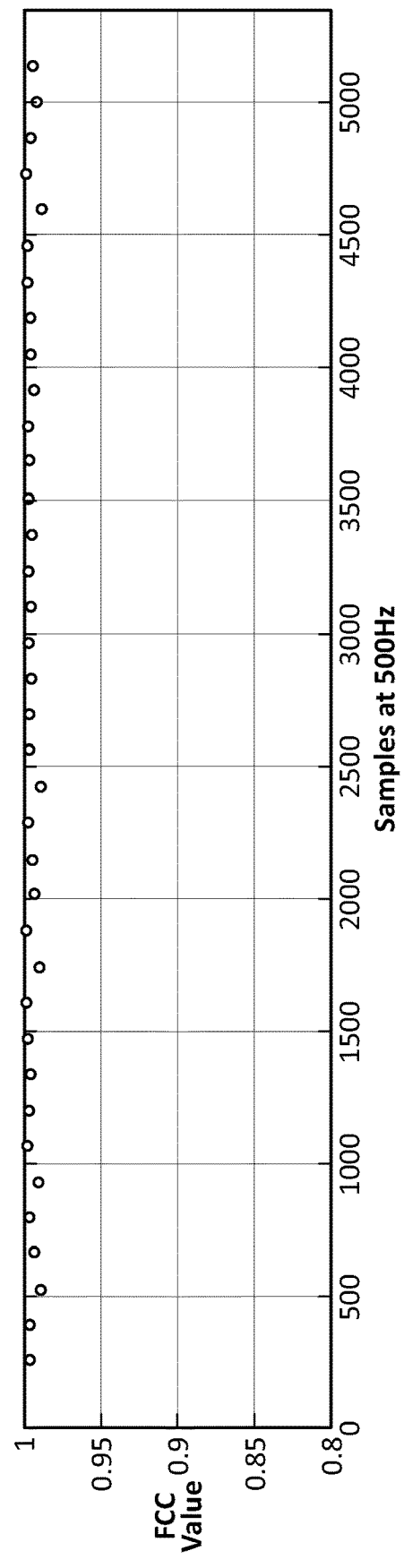
FIG. 8B illustrates a calculated FCC value for the MVT heartrate graph of FIG. 8A in accordance with exemplary embodiments described herein.

In some embodiments, the NSVT module 506 may detect NSVT based on the sustained duration of VT. For example, if VT lasts between 5 seconds and 15 seconds, it is considered non-sustained VT (NSVT). As shown in FIG. 8A, the VT episode is about 10.5 seconds, which indicates an NSVT episode. The circle in FIG. 8A indicates the QRS detection whereas the solid and dotted lines indicate ECG waveform and the R-wave detection threshold. FIG. 8B represents the calculated FCC value using circles. As shown, the FCC value is above 0.9 indicating a lack of QRS morphology variability which indicates a clear signal and a high correlation to the template. The short duration of VT combined with the clear signal is indicative of an NSVT episode.

The action module 504 may store episode information for later use. In some embodiments, the action module 504 may also transmit the episode data. For example, if the defibrillator 500 is connected to the internet, the action module 504 may upload episode and data to a secure location for physician review. The action module 504 may also take other steps unrelated to an NSVT episode, for example, the action module 504 may issue patient alerts, initiate a shock to the patient, and the like.

Figure 11:
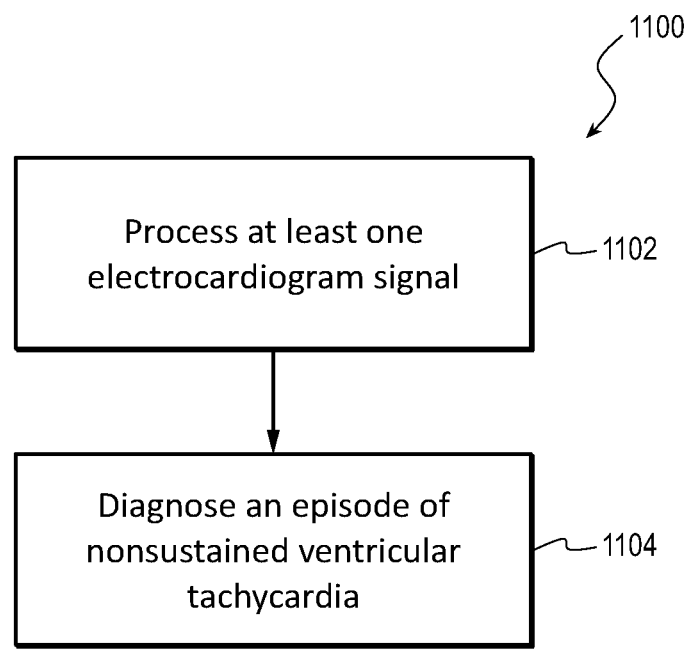
FIG. 11 is an exemplary flow diagram in accordance with exemplary embodiments described herein.

FIG. 11 is a flow chart illustrating an example of a method 1100 for WCD systems, in accordance with various aspects of the present disclosure. For clarity, the method 1000 is described below with reference to aspects of one or more of the systems described herein.

At block 1102, the method 1100 may process at least one electrocardiogram signal. For example, a defibrillator or other cardiac monitoring device may be in communication with at least two ECG electrodes. The at least one ECG electrode may be positioned to read a heartrate of a patient. The method 1100 may receive at least one signal from the ECG and process the signal. Processing the signal may include reading QRS impulses, heartrate, noise level, and the like.

At block 1104, the method 1100 may diagnose or flag an episode based at least in part on the processing of the at least one ECG signal. For example, the method 1100 may analyze the ECG signal for an NSVT time duration or threshold and a QRS criterion. When the ECG signals satisfies both the time duration and the QRS criterion, the method 100 may save episodic information for later review as a potential NSVT episode. The time threshold may be brief. For example, the NSVT time threshold may be between 5 seconds and 15 seconds. In some embodiments, the method 1100 may use a QRS template as the QRS criterion. For example, in some embodiments, the method 1100 may use the first few QRS complexes to form a temporary QRS template. If the following QRS signals from the ECG signal match or substantially match the temporary QRS template, the method 1100 may determine the signal is free of noise and the patient is experiencing an NSVT episode. In other embodiments, the method 1100 may additionally or alternatively compare the incoming QRS complexes to the NSR QRS template. If the incoming complexes substantially match the NSR QRS template, the method 1100 may determine an SVT episode is potentially occurring. Regardless, the QRS stability ensures the method 1100 is receiving a clear signal.

In some embodiments, the method 1100 may flag an NSVT episode when the ECG signal exceeds a heart rate threshold and the NSVT time threshold. The heart rate threshold may be greater than 170 BPM. If the patient is experiencing a high heart rate for a short duration, this is categorized as nonsustained VT and the episodic information is saved for later review.

In some embodiments, the method 1100 may flag an NSVT episode by examining QRS complexes. For example, in some embodiments, the method 1100 may analyze the normal sinus rhythm (NSR) QRS complexes and develop an NSR QRS template (See FIG. 9). If the NSR template does not match incoming QRS complexes, the method 1100 may determine that an event is happening. The event may include a noisy signal or may include a cardiac event. To differentiate, the method 1100 may analyze the incoming QRS complexes to determine if they are consistent. If the incoming QRS complexes are consistent, the method 1100 may develop a temporary QRS template and compare subsequent QRS complexes to the temporary QRS template. If the subsequent complexes match the temporary template, the method 1100 may record and flag the episode for a NSVT episode.

In some embodiments, the method 1100 may flag an NSVT episode by reviewing R-R stability. Noise generally causes false QRS detections, which creates heartrate variability, or R-R variability. R is a point corresponding to the peak of the QRS complex of the ECG wave, and R-R is an interval between success R points. R-R intervals are considered stable if the difference between two consecutive R-R-intervals is less than 20 milliseconds. Therefore, the R-R stability criterion is satisfied when a difference between at least two consecutive R-R intervals is less than 20 milliseconds.

Thus, the method 1100 may provide for storing potential episodes of NSVT. It should be noted that the method 1100 is just one implementation and that the operations of the method 1000 may be rearranged or otherwise modified such that other implementations are possible.

Figure 12:
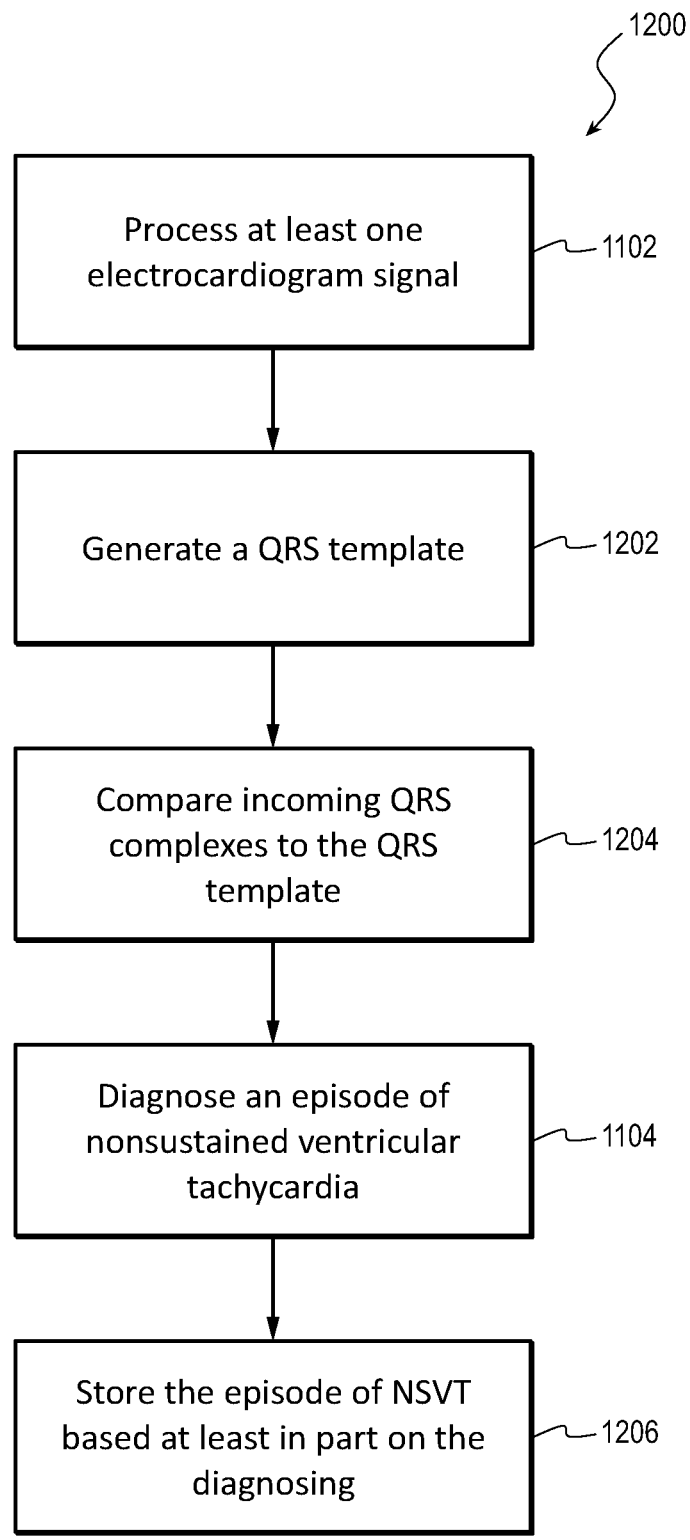
FIG. 12 is another exemplary flow diagram in accordance with exemplary embodiments described herein.

FIG. 12 is a flow chart illustrating an example of a method 1200 for WCD systems, in accordance with various aspects of the present disclosure. For clarity, the method 1200 is described below with reference to aspects of one or more of the systems described herein.

At block 1102, the method 1200 may analyze at least one ECG signal. At block 1202, the method 1200 may generate a temporary QRS template using the first few QRS complexes of a suspected episode. Once a temporary QRS template is generated, at block 1204, the method 1200 may compare incoming QRS complexes to the temporary QRS template. If the QRS morphology varies greatly between incoming QRS complexes and the normalized QRS template, the method 1200 may determine the signal contains noise and not track an NSVT episode. In some embodiments, the method 1200 may analyze the at least one ECG signal to determine if the incoming QRS complexes correlate to the NSR template as mentioned previously.

However, if the incoming QRS complexes substantially match the temporary QRS template, resulting in a low morphology, the method 1200 may determine the signal is good and at block 1104, diagnose or flag an episode of NSVT. Then at block 1206, the method 1200 may store the episode of potential NSVT based at least in part on the diagnosing. This may enable doctors and clinicians to later review the episode information and determine the patient may be at risk to develop sustained VT.

Thus, the method 1200 may provide for storing potential episodes of NSVT. It should be noted that the method 1200 is just one implementation and that the operations of the method 1200 may be rearranged or otherwise modified such that other implementations are possible.

A person skilled in the art will be able to practice the present invention after careful review of this description, which is to be taken as a whole. Details have been included to provide a thorough understanding. In other instances, well-known aspects have not been described, in order to not obscure unnecessarily this description.

Some technologies or techniques described in this document may be known. Even then, however, it is not known to apply such technologies or techniques as described in this document, or for the purposes described in this document.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to", "adapted to" and/or "configured to" denote one or more actual states of construction, adaptation and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Incorporation by reference: References and citations to other documents, such as patents, patent applications, patent publications, journals, books, papers, web contents, have been made throughout this disclosure. All such documents are hereby incorporated herein by reference in their entirety for all purposes.

Parent patent applications: Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

Reference numerals: In this description a single reference numeral may be used consistently to denote a single item, aspect, component, or process. Moreover, a further effort may have been made in the preparation of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and subcombinations of elements, features and acts or operations, which are regarded as novel and non-obvious. The claims also include elements, features and acts or operations that are equivalent to what is explicitly mentioned. Additional claims for other such combinations and subcombinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that the claim can have one or more of this component or this item.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

What is claimed is:

1. A method of providing targeted therapy to a heart of a patient based on determination of a category of cardiac episodes, the method comprising:
   receiving, by a processor, a first electrocardiogram (ECG) signal from one or more external electrodes;
   receiving, by the processor, a second ECG signal from the one or more external electrodes;
   detecting, by the processor, a first QRS complex in the first ECG signal;
   detecting, by the processor, a second QRS complex in the second ECG signal;
   calculating, by the processor, a Feature Correlation Coefficient (FCC) based, at least in part, on the first QRS complex and the second QRS complex;
   determining, by the processor, that the first ECG signal and the second ECG signal are indicative of an episode of sustained ventricular tachycardia (SVT) based, at least in part, on the calculated FCC;
   and
   providing therapy to the heart of the patient based, at least in part, on a determination that the episode of SVT is indicated.

2. The method of claim 1, wherein the episode of SVT is detected, at least in part, when a QRS criterion is satisfied.

3. The method of claim 2, wherein the QRS criterion comprises satisfying a FCC threshold between a temporary QRS template formed using at least two sequential QRS complexes and a subsequent QRS complex.

4. The method of claim 3, wherein calculating the FCC comprises calculating a similarity between at least one of the first QRS complex or the second QRS complex and the temporary QRS template.

5. The method of claim 1, wherein the episode of SVT is detected, at least in part, when a series of detected QRS complexes comprising the first QRS complex and/or the second QRS complex has a similar normal sinus rhythm (NSR) morphology.

6. The method of claim 1, further comprising:
   storing the episode of SVT based, at least in part, on the determining.

7. A method of categorizing cardiac episodes for treatment of a heart of a patient, the method comprising:
   processing at least one electrocardiogram (ECG) signal received from an external electrode;
   generating a temporary QRS template of two sequential incoming QRS complexes from the ECG signal;
   determining a similarity between the temporary QRS template and at least two subsequent QRS complexes by calculating a feature correlation coefficient (FCC) between the temporary QRS template and the subsequent QRS complexes;
   categorizing an episode as potential non-sustained ventricular tachycardia (NSVT) or a sustained ventricular tachycardia (SVT) based, at least in part, on the similarity between the temporary QRS template and the at least two subsequent QRS complexes;
   storing the categorized episode of potential NSVT; and
   accessing the categorized episode of potential NSVT to determine a risk for the patient to develop SVT, the determination of the risk of SVT resulting in providing therapy for the treatment of the heart of the patient.

8. The method of claim 7, wherein the episode of potential NSVT is categorized based, at least in part, on when an NSVT time duration and a QRS criterion are satisfied.

9. The method of claim 8, wherein the NSVT time duration is between 5 seconds and 15 seconds.

* * * * *